United States Patent

Makaran

[11] Patent Number: 5,103,807
[45] Date of Patent: Apr. 14, 1992

[54] SHAPE MEMORY ALLOY ORTHOTIC DEVICE

[76] Inventor: John Makaran, 204 Gladstone Avenue, London, Ontario, Canada, N5Z 3R9

[21] Appl. No.: 692,345

[22] Filed: Apr. 26, 1991

[51] Int. Cl.⁵ ............................................. A61H 1/02
[52] U.S. Cl. ...................................... 128/26; 606/78; 602/21
[58] Field of Search .................. 606/78; 623/25, 24, 623/63, 64, 65; 128/26, 77, 87 A, 89 R; 901/36

[56] References Cited

U.S. PATENT DOCUMENTS

| | | | |
|---|---|---|---|
| 2,553,277 | 5/1951 | Robinson et al. | 128/26 |
| 3,707,963 | 1/1973 | Keropian | 128/77 |
| 3,756,222 | 9/1973 | Ketchum | 128/26 |
| 4,246,661 | 1/1981 | Pinson | 623/25 |
| 4,665,906 | 5/1987 | Jervis | 606/78 |
| 5,062,855 | 11/1991 | Rincoe | 623/24 |

Primary Examiner—Richard J. Apley
Assistant Examiner—Susan L. Weinhoffer
Attorney, Agent, or Firm—Joseph A. Day

[57] ABSTRACT

There is disclosed an orthotic device adapted for use with a hand of a user to restore grasping function. The device includes a finger retaining member and thumb support. The finger retaining member is pivotally moveable from a first open or non-grasping position when the finger retaining member is spaced from the thumb support, to a second position where the two are adjacent. The device achieves this function by incorporating a suitable shape memory alloy suitably associated with the finger retaining member and thumb support.

23 Claims, 4 Drawing Sheets

SHAPE MEMORY ALLOY ORTHOTIC DEVICE

FIELD OF THE INVENTION

This invention relates to orthotic devices and more particularly relates to such devices incorporating shape memory alloy elements to actuate the device.

BACKGROUND OF THE INVENTION

The present invention provides an orthotic device incorporating a shape memory alloy element as the actuation means. Generally, the shape memory of an alloy involves a transformation in the metal from a low temperature disorganized crystal structure to a high temperature highly ordered crystal structure. The phase transformation occurs at a specific temperature. Thus, if a metal has been "programmed" with a certain memory shape and is deformed at a low temperature, the metal will recover its memory shape when heated above the transition temperature. A material having such properties is particularly useful in a diverse range of applications. One such application is illustrated in U.S. Pat. No. 4,553,393. In this document, Ruoff discloses an actuator incorporating a shape memory alloy. The actuator provides torque or force directly to a load to eliminate the use of motors or transmissions, etc. conventionally used to achieve the same result.

Further, Jamieson, in U.S. Pat. No. 4,665,334 discloses a rotary stepping device which includes a shape memory metal as a main drive unit for a motor. The memory metal provides drive motion to a spring clutch. The clutch is positioned about a shaft and when the metal is actuated, the clutch tightens effecting rotation of a shaft of the motor. Although useful devices, the prior art is not directed to medical applications. The present invention permits a quadriplegic or similarly disabled person to regain grasping function. By employing a shape memory alloy in an orthotic device, the user can simply and expediently grasp and release an object without any undue discomfort or with the use of a complicated apparatus.

SUMMARY OF THE INVENTION

The present invention is directed to an orthotic device using a shape memory alloy element e.g. Nitinol adapted for wear about the hand and at least a portion of the forearm of a user. The device is particularly useful for handicapped users, particularly quadriplegics since it provides grasping function for the user. The device, in one embodiment, includes a support member adapted for wear about the forearm of a user which extends into finger retaining means and thumb support means. The support member and thumb support means preferably comprise a malleable material which is readily conformable to a user's hand and arm e.g. aluminum, plastic etc. The members may include suitable padding, for example, polyurethane foam to ensure comfort; the device will be held in place by straps. The finger retaining means comprises an open inclined framework e.g. a shell, which allows retention of at least one finger of the user therein. It is additionally associated with pivot means, which pivot the finger retaining means from a first open or non-grasping position where the finger retaining means is spaced from thumb supporting means, to a second closed or grasping position where the same is adjacent the thumb supporting means.

The pivot means of the present invention comprises, in one form, a rotary ratchet, rotatably mounted on the support member of the device, which is connected to and activatable by the shape memory alloy. The shape memory element is preferably in communication with an electrical source such that upon passing electrical current through the shape memory alloy element, the element is altered in length thus effecting pivoting of the pivot means which, in turn, effects movement of the finger retaining means. The device further includes means for limiting and stopping the rotation of the pivot means e.g. a shape memory alloy activatable pawl member having a projecting element adapted to releasably engage the rotary ratchet.

Retraction of the finger means from the grasping position to the non-grasping position is achieved by a spring or antagonistic shape memory element associated with the rotary ratchet. Once the stop means i.e. projecting element of the pawl member is disengaged from the rotary ratchet, the spring will release the finger retaining means to an open position.

The current source which activates the shape memory alloy is triggered by suitable switching means. In one form, the switching means may comprise an orally activatable device, eg. a sip and puff switch which the user may employ to trigger the current. In another form, the triggering may be achieved through the use of a myoelectric switching means which relies on electrical impulses from operative muscles. The signal is picked up by electrodes attached to the skin of a user which is amplified to produce a voltage. This voltage is subsequently transmitted through circuitry to deliver a current through the shape memory alloy element. The shape memory alloy element preferably is an elongated length, although numerous other forms are contemplated. In another embodiment, the shape memory alloyactuation means of the present invention may include both an elongated length and a shape memory alloy spring.

In a further embodiment, the actuation means comprises a plurality of shape memory alloy springs.

In still further embodiments, the thumb supporting means and finger retaining means may both comprise a shape memory alloy, which could be made to respond to electrical stimulation for mutual movement thereby eliminating the use of a pivot means. Additionally, the switching means may be arranged to respond to head movements of a user or may incorporate a voice command system for linkage therewith.

It will be readily understood that the invention may be easily modified for application with the forearm to permit movement at the elbow, as well as to other dysfunctional limbs and such modifications are well within the scope of the present invention.

Clearly, there has been a need for such an orthotic device since the advent of shape memory alloy technology and, accordingly, it is an object of the present invention to provide such a device.

It is a further object of one embodiment of the present invention to provide an orthotic device adapted for placement about the hand and at least a portion of the forearm of a user, the device comprising:

a support member adapted for placement about at least a portion of a user's forearm;

finger retaining means operatively associated with support member for retaining at least one finger of a user;

thumb support means associated with the finger retaining means for supporting a thumb of a user;

pivot means in operative association with the finger retaining means for effecting pivoting movement of the finger retaining means from a first non-grasping position wherein the finger retaining means is spaced from the thumb support means to a second grasping position wherein the finger retaining means is adjacent the thumb supporting means with actuation means in operative association with the pivot means, the improvement wherein the actuation means comprises at least one shape memory alloy element.

A further object of the present invention is a method of actuating an orthotic device having finger retaining means, thumb supporting means and pivot means in operative association with the finger retaining means, the improvement comprising the steps of:

providing a shape memory alloy element in operative association with the finger retaining means;

passing an electrical current through the shape memory element; and effecting movement of the finger retaining means from a first non-grasping position spaced from the thumb supporting means to a second grasping position wherein the finger retaining means is adjacent the thumb support means.

Yet another object of the present invention provides the use of a shape memory alloy element for activating an orthotic device, the device being adapted for placement about the hand and at least a portion of the forearm of a user.

In yet another object of one embodiment of the present invention, there is provided an orthotic device which is easily operated by switching means.

In a further object of the present invention, there is provided an orthotic device which is operated myoelectrically.

Yet another object of the present invention is to provide an orthotic device which does not employ complicated actuation means.

A further object of the present invention is to provide an orthotic device which is light-weight to prevent fatigue during use.

A still further object of the present invention is to provide an orthotic device which includes proportional control for grasping objects.

Having thus generally described the invention, reference will now be made to the accompanying drawings, illustrating preferred embodiments.

DETAILED DESCRIPTION OF THE PREFERRED EMBODIMENTS

Figure 1:
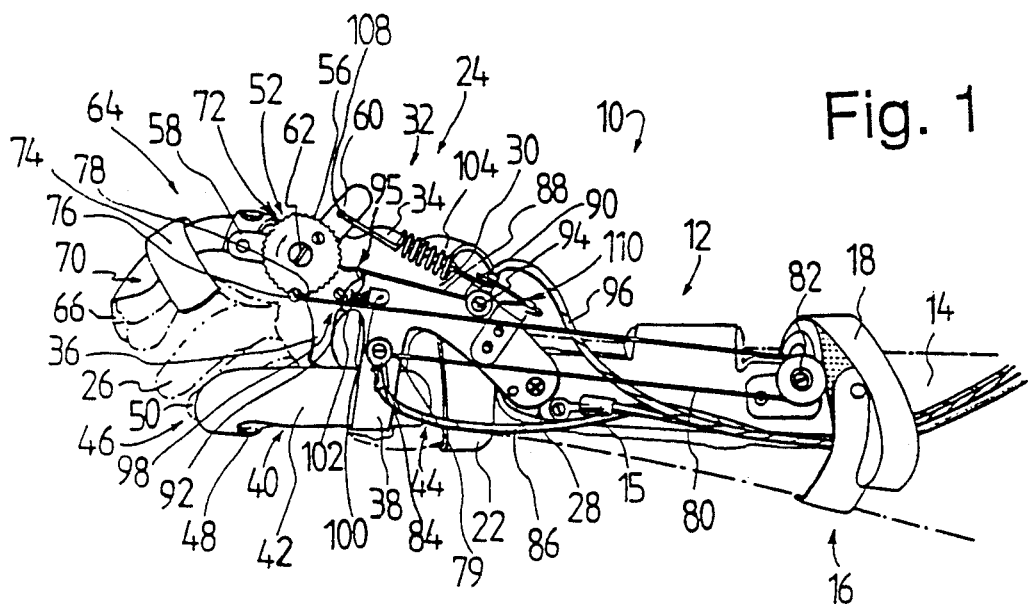
FIG. 1 is a side view of one embodiment of the present invention illustrating the device in an open non-grasping position.

Referring to FIG. 1, shown is a side view of the device of the present invention generally indicated by numeral 10. The device 10 comprises a support member 12 adapted for placement about the forearm 14 of a user. The support member 12 includes a forearm strap 18 proximate end 16 thereof and a user strap 22 proximate end 20. Each of the straps 18 and 22 effectively mount support member 12 about in an adjustable and releasable manner to thereby retain a user's forearm 14 by virtue of suitable fastening means which are preferably selected from those which are not unduly complicated to remove e.g. Velcro (trade mark) straps. Proximate end 20 of support member 12 there is a structure 24 shown in one form for fitting about the hand 26 of a user fixedly secured thereto at end 28 thereof. The structure 24 may be secured to support member 12 by any suitable means e.g. welding, bolting, etc. The structure preferably includes a first upwardly inclined member 30 joined at an end 28 thereof to support member 12 as herein previously described while a second end 32 includes pivot means hereinafter described. Extending from and integrally associated with the first upwardly inclined member 30, substantially intermediate of ends 28 and 32 thereof is a further support member 34 which extends over the breadth of the top of hand 26 of a user. Similarly, a further support 36 integral with member 30 and proximate end 32 thereof extends across a user's palm. A further element 38 substantially intermediate of ends 28 and 32 of member 30 and integrally associated therewith, extends downwardly and connects by suitable means e.g. welding etc. to a thumb supporting means 40. The thumb supporting means, as illustrated in one possible form, includes a longitudinal member 42 connected proximate the end 44 thereof to member 38. The opposed end 46 of member 42 preferably includes an integral U-shaped segment 48 into which a user's thumb 50 is placed. The support members described herein preferably comprise a material which provides adequate strength, while being malleable enabling conformation about the hand and forearm of the user. Suitable padding, e.g. polyurethane foam may be secured to the members for contact against the user's skin thus ensuring comfort.

Figure 3:
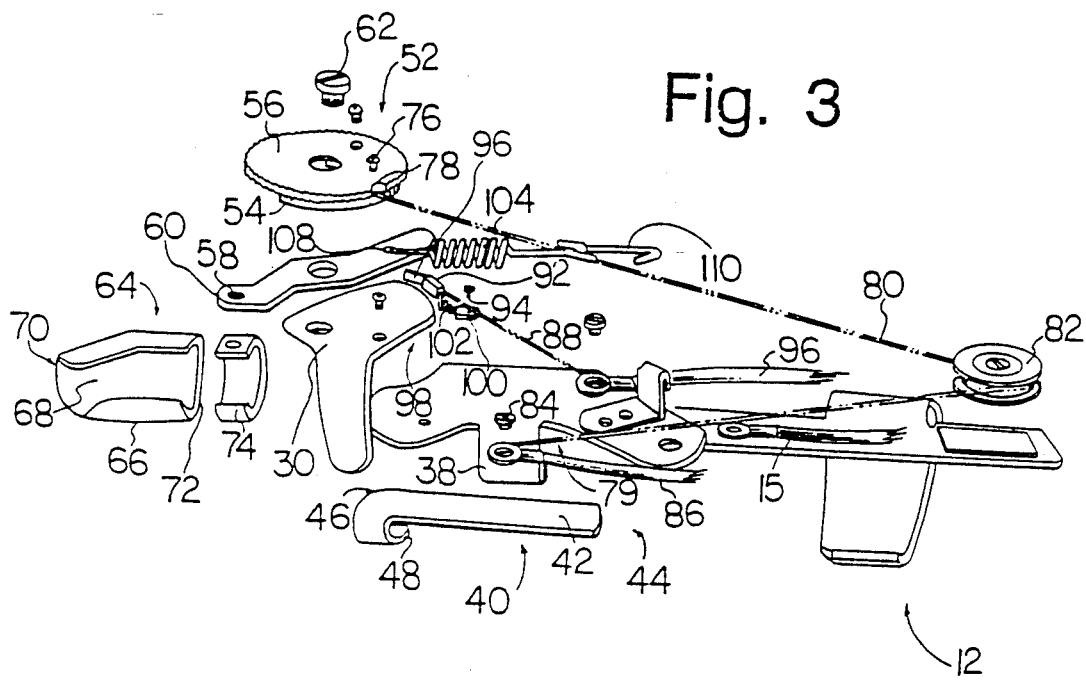
FIG. 3 is an exploded view of the embodiment illustrated in FIGS. 1 and 2.

The device 10, as briefly noted previously herein, provides pivot means 52. The pivot means 52 is preferably mounted to end 32 of the upwardly inclined member 30 for rotation thereon. The pivot means 52 preferably includes a spacer member 54 e.g. a washer which has concentrically mounted thereon a toothed wheel 56 e.g. a rotary ratchet (shown more clearly in FIG. 3). It is particularly preferred that intermediate spacer member 54 and rotary ratchet 56 there be included a laterally radiating element 58 which operatively associates the pivot means 52 with finger retaining means hereinafter described. Additionally, a second laterally radiating element 60 is provided the purpose of which will be further described hereinafter. Elements 58 and 60 are preferably spaced apart and are connected concentrically between spacer member 54 and rotary ratchet 56 by fastening means 62 e.g. a screw extending centrally therethrough to support member 30.

The finger retaining means 64 comprises in one form, an open elbowed shell 66 having an open top 68 and open spaced apart ends 70 and 72. The elbowed shell 66 preferably has a smooth elbowed inclination enabling the positioning of a user's fingers therein similar to the positioning thereof in a grasping position without any discomfort or unnatural depression of the fingers. It is preferred that the elbowed shell 66 accommodate at least one finger of a user and more desirably a plurality. In addition, the finger retaining means 64 may include a retaining element 74 for placement about the shell 66 and fingers of a user.

Referring to the pivot means 52, which communicates with finger retaining means 64 more specifically shell 66, it is particularly preferred that the pivot means 52 be capable of being activated by using a shape memory alloy. Generally, shape memory alloys are alloys deformable which can be returned to a predetermined shape size, length etc. at a specific temperature. The predetermined shape will not alter upon subsequent cooling. Having such properties, the use of a shape metal alloy is particularly preferred in the device of the present invention. It is preferred that the memory alloy employed in the present invention be selected from nickel-titanium (known in the art as NITINOL) copper-zinc or other such alloys employing the known shape memory crystal property, namely, a body-centered cubic lattice structure in an austenitic phase and a twinned, close-packed lattice structure in the martensitic phase.

The pivot means 52 preferably includes a fastening means 76 e.g. a screw etc. at a point spaced from elements 58 and 60 to permit connection of one end 78 a first shape memory element 80 for example, a wire or strand thereto. It is preferred that the strand 80 extend over a pulley 82. The pulley 82 is fixedly secured to support member 12. The other end 79 of strand 80 is fixedly secured to element 38 adjacent thumb supporting means 40 by a fastener 84. The fastener 84 further secures a first wire lead 86 thereto, the function of which will be disclosed hereinafter. Similar to the above, a second shape memory strand 88 is preferably included to aid in the operation of the device 10. One end 90 of the strand 88 is, as in the above previously mentioned arrangement, fixedly secured to a fastener 94 which further fastens a wire lead 96 to support 24. The other end 92 of strand 88 is preferably fixedly secured to stop means 95 of a pawl member 98. The pawl 98 includes a body 100 secured to support 24 adjacent pivot means 52. In addition, a ground wire lead 15 is fastened to the device in a convenient location in this embodiment and subsequent embodiments.

A biasing spring 102 projecting outwardly from within body 100 biases stop means 95 against the toothed rotary ratchet 56. A second bias spring 104 is connected to radiating element 60, of pivot means 52, by an aperture 108 extending therethrough. The spring 104 is connected at a second end thereof to an appropriate point on the device 10 by a suitable means 110 e.g. a clip, aperture, etc. An appropriate location is, for example, on support 30.

Figure 2:
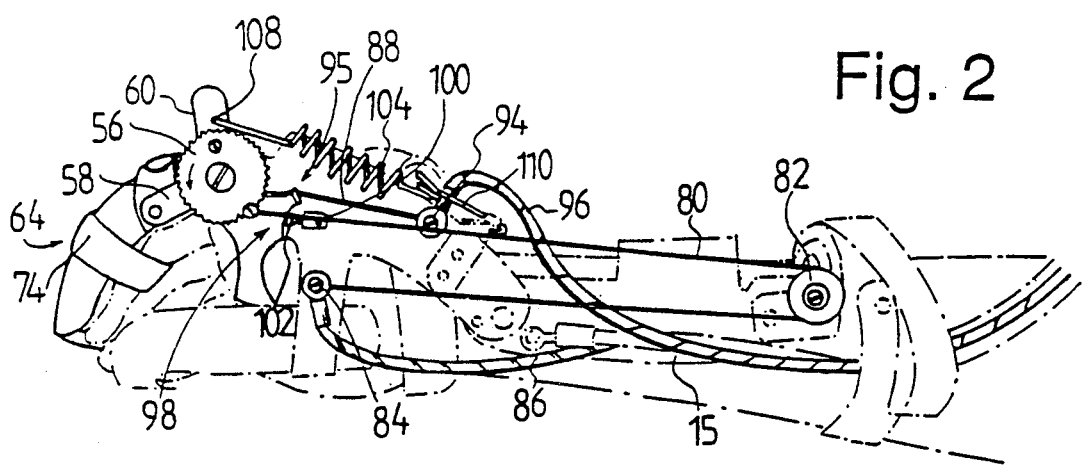
FIG. 2 is a side view of the embodiment of FIG. 1 in a closed or grasping position.

In operation, according to this embodiment of the present invention, the device is movable from a first non-grasping position, (FIG. 1) i.e. finger retaining means 64 is spaced from thumb supporting means 40 to a second grasping position (FIG. 2) where finger means 64 is adjacent thumb supporting means 40. This is achievable since the device incorporates a shape memory alloy as the actuation means. In order to achieve this grasping function, the user actuates the switching means (hereinafter described) which sends an electrical current through the wire lead 96 which is also in contact with end 90 of the shape memory element 88. Due to the high electrical resistivity of the shape memory alloy, the temperature of the element becomes elevated as electrical current passes therethrough. This effects, as a result of shape memory alloy properties, contraction i.e. a shortening in the length of the strand 88 thereby disengaging stop means 95 of pawl member 98 which, in turn, compresses bias spring 102. In order to operate the pivot means 56, an electrical current again supplied by switching means is passed to wire lead 86. The lead 86, as previously described, contacts end 79 of shape memory strand 80, while the strand 80 terminates at fastening means 76 of pivot means 52. Thus, having the stop means 95 disengaged from the rotary ratchet 56, the strand 80 contracts about pulley 82 due to heating from the current and causes the finger means to pivot downwardly to a point adjacent the thumb supporting means 40 (FIG. 2). In this position, the stop means 95 is engaged with the rotary ratchet to conserve power, which would otherwise be dissipated by memory strand 80 in holding the finger retaining means 64 in an upwardly inclined position. Additionally, in this position, bias spring 104 is wishes to release an object (not shown) being held, the user simply actuates the switching means to initiate a current passage into strand 88 thereby causing stop means 96 to disengage rotary ratchet 56. The finger retaining means 64 is then returned to a non-grasping position (FIG. 1) by the contraction of bias spring 104. Since the stop means 95 of pawl member 98 is associated with a shape memory strand, the stop means may be engaged with the rotary ratchet 56 selectively by a user to thus provide proportional grasping force or pressure. This feature is particularly useful when a user wants to pick up thin objects or when squeezing, for example, a toothpaste tube.

Figure 4:
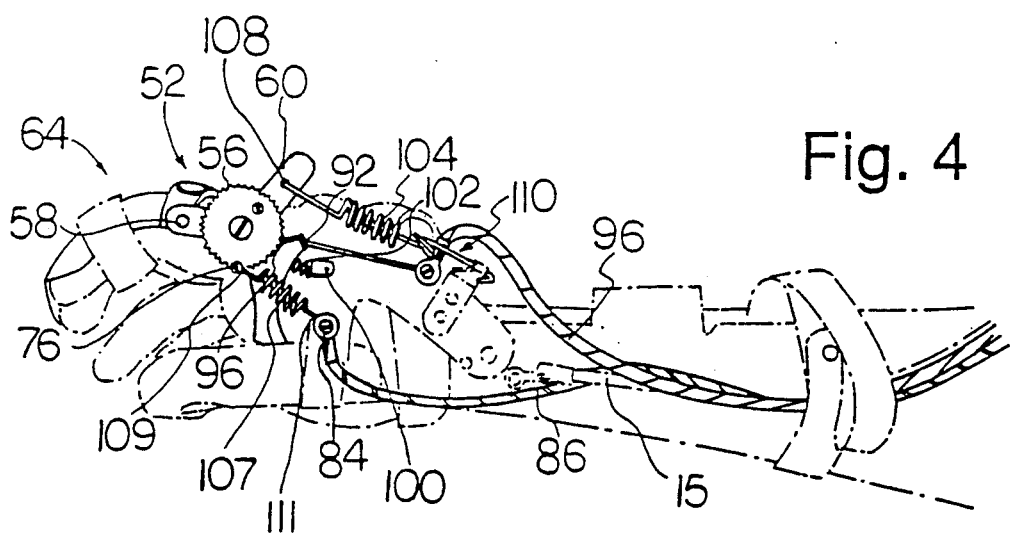
FIG. 4 is a side view of the present invention according to another embodiment.

Turning now to FIG. 4, shown is an alternate embodiment of the present invention. Similar numerals apply to similar components from previous figures. In this embodiment, the shape memory strand 80 is replaced with a shape memory spring 107. The spring 107 is preferably connected at one end 109 to fastening means 76 of pivot means 52 while end 111 is connected with fastener 84 enabling electrical stimulation through wire lead 86. In this arrangement, the spring 107 is slightly stretched between the connection sites at pivot means 52 and fastener 84 thus allowing contraction thereof upon electrical stimulation which, in turn, will cause rotation of pivot means 52 to move the finger retaining means 64.

Figure 5:
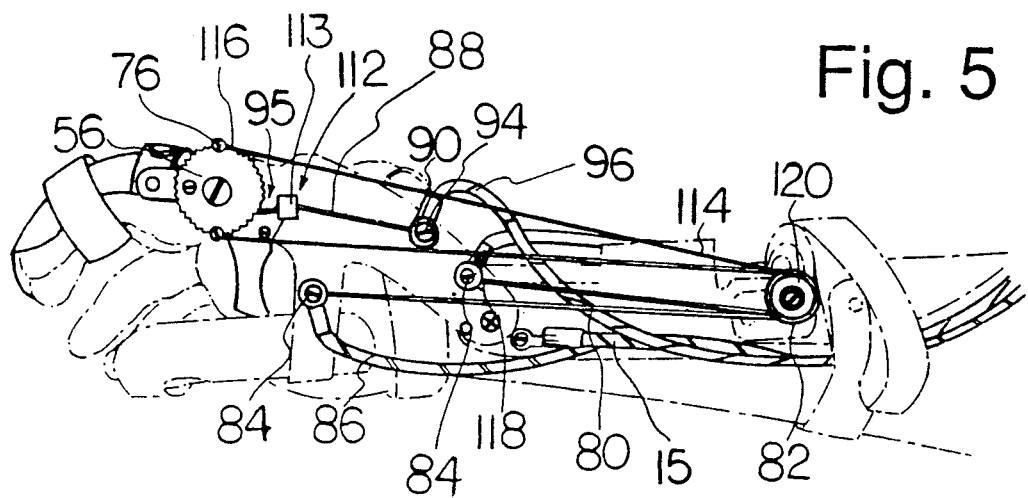
FIG. 5 is a side view of the present invention according to yet another embodiment.

Referring now to FIG. 5, shown is a side view of yet another embodiment of the present invention. Once again, similar numerals will be used to indicate similar components in this embodiment. In the embodiment illustrated, the mechanics of operation of the device 10 are modified to include a two way acting pawl 112 and a further second shape memory strand 114 in addition to strand 80. In this embodiment, bias spring 104 and projecting element 60 are removed. The second memory strand 114 is connected at one end 116 thereof to the rotary ratchet 56 of pivot means 52 by similar fastening means 76 by a screw etc. as that in the embodiment of FIG. 1. The strand 114 preferably communicates with a pulley 120 which may be mounted concentrically and freely rotatably on pulley 82. Pulley 120 may additionally be independent of pulley 82 and rotatably mounted at a convenient location on the device 10. The second end 118 of strand 114 is, in one possible embodiment, fastened to the device 10 by suitable fastening means such as those herein previously described e.g. fastener 84 as illustrated in FIG. 1. It will be understood that the fastener 84 fastens a third wire lead 120 for connection therewith in a convenient location as illustrated in the Figure.

The pawl 112, in this embodiment, is preferably two-way. In this form, stop means 95 communicates with a tension spring (not shown) with which it is connected, while additionally being connected with a shape memory alloy spring (not shown). The stop means 95 is connected with the tension and shape memory springs such that it slides axially within the body 113 of the pawl member 112 for engagement and disengagement with the rotary ratchet 56. In this embodiment, wire lead 96 may be directly connected for electrical contact with pawl member 112 thus eliminating shape memory strand 88.

In operation of this embodiment of the invention, the device is moved to a closed position, i.e. such as that shown in FIG. 1, by first triggering the switching means (hereinafter described) to send an electrical current to wire lead 96 which causes shape memory spring within pawl member 112 to contract. Upon contraction, stop means 95 is disengaged from rotary ratchet 56. The stop means 95 is held out of engagement until such time that the device is either in a grasping or non-grasping position. At this point, shape memory strand 80 is electrically stimulated, thus contracting and directing the finger retaining means 64 downwardly as previously described herein. Once the grasping position is complete, the shape memory spring of pawl member 112 is out of electrical contact, the tension spring then urges the stop means 95 back into engagement with rotary ratchet 56. During the grasping movement, strand 114 stretches to accommodate the motion. In order to release, i.e. move the device 10 into non-grasping position, the user reactivates the pawl member as previously described to thereby disengage the same while strand 114 is electrically stimulated by a current through wire lead 120. This allows the strand 114 to contract to thereby cause pivot means 52 to pivot operably to effect the non-grasping position. The pawl 112 may then be reengaged to retain this position of the finger means 64.

Figure 6:
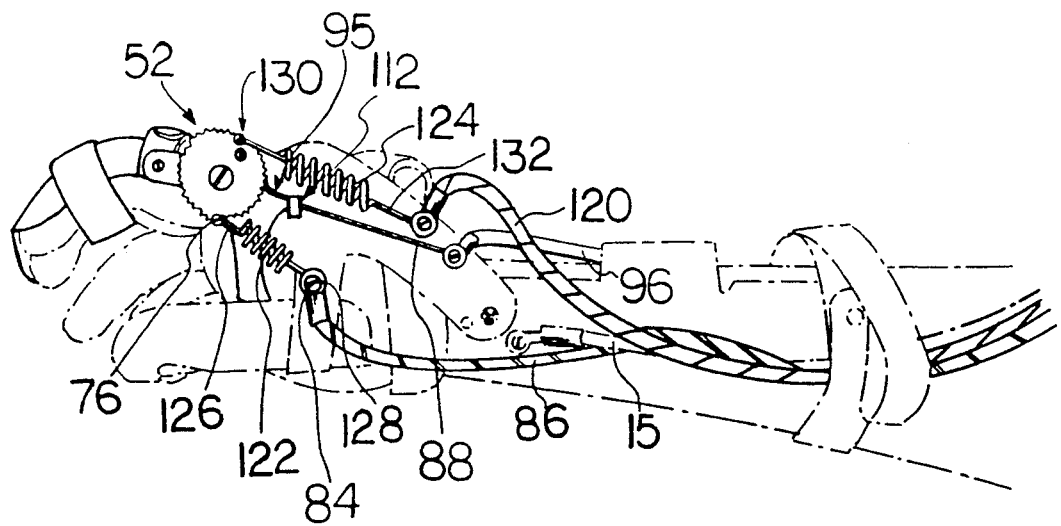
FIG. 6 is a side view of the present invention according to still another embodiment.

Referring to FIG. 6, shown is a side view of yet another embodiment of the present invention. In this embodiment, a similar pawl member 112 is incorporated. The embodiment illustrated replaces the shape memory strands 114 and 80 of FIG. 5 with two shape memory alloy springs. The springs 122 and 124, in one possible arrangement, may be associated with the pivot means 52 as illustrated in FIG. 6. Spring 122 is connected at end 126 thereof to fastener means 76 as described previously herein while end 128 communicates with wire lead 86 via fastener 84.

Similarly, spring 124 is connected at end 130 either directly to rotary ratchet 56 of pivot means 52 or alternatively, to element 60 projecting therefrom. The other end 132 of spring 124 is connected for electrical contact with wire lead 120 in a similar manner as illustrated in FIG. 5. The springs 122 and 124 are preferably slightly stretched so that when activated they contract to effect their respective motion of finger means 64. The operation steps of this embodiment are similar to those outlined for the embodiment of FIG. 5.

In further embodiments, the entire finger means 64 and thumb supporting means 40 may be composed of a shape memory alloy which could be made to respond to electrical stimulation for mutual movement to a grasping position thus eliminating the pivot means 52, pulleys 82 etc.

Figure 7:
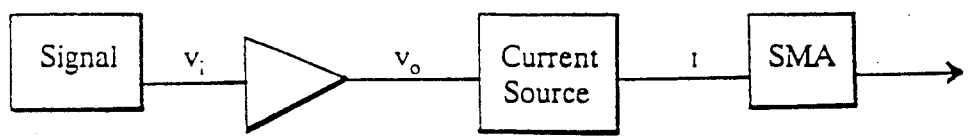
FIG. 7 is a diagrammatic representation of the switching circuit according to one embodiment.

Turning to the switching means used in order to send current to the shape memory elements used in the present invention, two such arrangements are contemplated namely: (i) a sip and puff switching means and (ii) myoelectric control. Referring initially to the sip and puff switching means, FIG. 7 illustrates a block diagrammatic representation of a circuit used for such a switch arrangement.

The signal is initiated by a suitable oral device (not shown) which the user controls. The user then "puffs" in the tube which is sensed by a suitable element e.g. a flexible diaphragm which responds to positive air pressure in the case of "puffing" or negative air pressure in the case of "sipping" which is received at 134. The signal is transferred into a voltage and passed to suitable processing circuitry 136. The voltage is passed further to a current source 138 e.g. Nickel cadmium batteries etc. wherein the current is delivered to the appropriate wire leads e.g. 80, 88, 120, etc. as herein previously described to effect the movement of the device by shape memory alloy stimulation. In the embodiment of FIGS. 4, 5 and 6, three of these circuits is required i.e. one to actuate the strand for opening the device to a non-grasping position, one to actuate the strand responsible for grasping motion, while another is dedicated to the operation of the pawl. In the embodiment illustrated in FIGS. 1 through 3, only two such circuits are required, namely, one for closing and one for operation of the pawl. The opening is achieved through the use of the non-shape memory alloy bias spring of that embodiment. The circuitry of the switching means may be suitably modified so that the outputs of the circuit could be latched or coupled thus allowing a user more freedom since actuation by constant puffing or sipping would be eliminated. In addition, the circuit may include sample and hold features wherein the force of grip of the device would be proportional to the extent to which the user sips or puffs.

Referring to myoelectric actuation, the device 10 may, depending on the capabilities of the user, be actuated by employing this technology as is known in the art.

Figure 8:
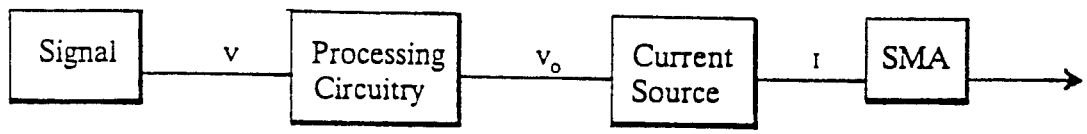
FIG. 8 is a diagrammatic representation of the switching circuit according to another embodiment.

Generally, this type of actuation relies on electrical impulses from functioning muscles. These impulses are contacted via a network of surface electrodes (not shown) to the shin of a user. The circuit useful for this type of control is illustrated in FIG. 8. The signal 140 from the electrodes is amplified by high gain amplifiers 142 to produce a voltage V. The voltage V then triggers a suitable current source 144 as described previously in the puff and sip arrangement of FIG. 7. This current, I, is then sent to the leads of the device for actuation of the shape memory alloy components. Although these switching means for actuation of the shape memory elements are preferred, the invention is not limited to these methods. Many devices are contemplated, for example as previously noted herein, the user may actuate the strands by a suitable arrangement which responds to head movements of a user, or further a voice command system may be employed.

As those skilled in the art will realize, these preferred illustrated details can be subjected to substantial variation, without affecting the function of the illustrated embodiments. Although embodiments of the invention have been described above, it is not limited thereto and it will be apparent to those skilled in the art that numerous modifications form part of the present invention insofar as they do not depart from the spirit, nature and scope of the claimed and described invention.

We claim:

1. An orthotic device adapted for placement about the hand and at least a portion of the forearm of a user, said device comprising:
   a support member adapted for placement about at least a portion of a user's forearm;
   finger retaining means operatively associated with support member for retaining at least one finger of a user;
   thumb support means associated with said finger retaining means for supporting a thumb of a user;
   pivot means in operative association with said finger retaining means for effecting pivoting movement of said finger retaining means from a first non-grasping position wherein said finger retaining means is spaced from said thumb support means to a second grasping position where said finger retaining means is adjacent said thumb supporting means, and actuation means in operative association with said pivot means, the improvement wherein said actuation means comprises a shape memory alloy element.

2. The orthotic device as defined in claim 1, wherein said shape memory alloy element is an elongated length of said shape memory alloy.

3. The orthotic device as claimed in claim 2, wherein said shape memory alloy element is a shape memory spring.

4. The orthotic device as claimed in claim 2, wherein said shape memory alloy element comprises a combination of at least one spring and at least one elongated length.

5. The orthotic device as defined in claim 1, wherein said shape memory alloy element is to capable of being actuated by heating.

6. The orthotic device as defined in claim 5, wherein said shape memory alloy element is an alloy contractible upon heating.

7. The orthotic device as defined in claim 1, wherein aid shape memory alloy element is further connected to a source of electrical current.

8. The orthotic device as claimed in claim 1, wherein aid device further includes a pawl member.

9. The orthotic device as claimed in claim 8, wherein said pawl member is capable of being actuated by said actuation means.

10. The orthotic device as claimed in claim 9, wherein said pawl member includes stop means.

11. The orthotic device as claimed in claim 10, wherein said stop means is in operative association with a shape memory alloy element.

12. The device as claimed in claim 11, wherein said pivot means is connected with shape memory alloy spring.

13. An orthotic device actuable by a shape memory alloy element comprising:
    a support member adapted for placement about a user's hand and at least a portion of a user's forearm;
    finger retaining means for retaining at least one finger;
    thumb support means associated with said finger retaining means for supporting a thumb of a user;
    rotary ratchet means in operative association with said finger retaining means and a shape memory alloy element, said rotary ratchet being adapted to rotate said finger retaining means from a first non-grasping position wherein said finger retaining means is adjacent said thumb support means to a grasping position wherein said finger retaining means is adjacent said thumb support means; and
    means releasably engageable with said rotary ratchet means for limiting the rotation of said rotary ratchet;
    whereby upon stimulation of said shape memory alloy element, said rotary ratchet rotates said finger retaining means from a first non-grasping position wherein said finger retaining means is adjacent said thumb support means to a second grasping position wherein said finger retaining means is adjacent said thumb support means.

14. In a method of actuating an orthotic device having finer retaining means, thumb supporting means and pivot means in operative association with said finger retaining means, the improvement comprising the steps of:
    providing a shape memory alloy element in operative association with said finger retaining means; and
    passing an electrical current through said shape memory alloy element including movement of said finger retaining means is effected from a first non-grasping position spaced from said thumb supporting means to a second grasping position so that said finger retaining means is adjacent said thumb support means.

15. The method as defined in claim 14, further including the step of providing a shape memory alloy in operative association with means for limiting the motion of said pivot means.

16. The method as defined in claim 15, further including the step of passing electrical current through said shape memory alloy element.

17. The method as defined in claim 15, wherein said means for limiting the motion of said pivot means includes a pawl member.

18. The method as defined in claim 15, wherein said pawl member includes a shape memory alloy spring therein.

19. The method as defined in claim 14, further including a step of triggering switching means for delivery of current to said shape memory alloy element.

20. The method as defined in claim 19, wherein said switching means comprises a sip and puff switching means.

21. The method as defined in claim 19, said switching means comprises myoelectric switching means.

22. The method as defined in claim 14, wherein said shape memory alloy element is a wire.

23. The method as defined claimed in claim 14, wherein said shape memory alloy element is a spring.

* * * * *